(12) United States Patent
Lo et al.

(10) Patent No.: US 7,648,717 B2
(45) Date of Patent: Jan. 19, 2010

(54) HERBAL EXTRACT HAVING ANTI-VIRUS ACTIVITY AND PREPARATION OF SAME

(75) Inventors: Li-Ching Lo, Miaoli County (TW); Lien-Tai Chen, Taoyuan (TW)

(73) Assignee: Industrial Technology Research Institute, Hsinchu (TW)

( * ) Notice: Subject to any disclaimer, the term of this patent is extended or adjusted under 35 U.S.C. 154(b) by 20 days.

(21) Appl. No.: 12/219,795

(22) Filed: Jul. 29, 2008

(65) Prior Publication Data

US 2008/0286849 A1 Nov. 20, 2008

Related U.S. Application Data

(63) Continuation-in-part of application No. 11/518,252, filed on Sep. 11, 2006, now abandoned.

(51) Int. Cl.
*A61K 36/00* (2006.01)
(52) U.S. Cl. ..................................... 424/725
(58) Field of Classification Search ........................ None
See application file for complete search history.

(56) References Cited

U.S. PATENT DOCUMENTS 5,888,527 A 3/1999 Nashimoto 6,214,350 B1 4/2001 Hwang
2002/0164367 A1 11/2002 Liu
2004/0253331 A1 * 12/2004 Lo et al. ..................... 424/769

FOREIGN PATENT DOCUMENTS

CN 1122711 A * 5/1996

OTHER PUBLICATIONS

Du et al. Deparation of Bioactive Quadri-Terpenic Acids From the Fruit of Ligustrum Lucidum AIT by High-Speed Countercurrent Chromatography; Journal of Liquid Chromatography (1995) 18 (10), pp. 1997-2004.
Niikawa et al. Isolation of Substances from Glossy Privet (Ligustrum Lucidum AIT.) Inhibiting the Mutagenicity of Benzo[A]Pyrene in Bacteria; Mutation Research, 319 (1993) pp. 1-9.

* cited by examiner

*Primary Examiner*—Patricia Leith
(74) *Attorney, Agent, or Firm*—Bacon & Thomas, PLLC

(57) ABSTRACT

The invention relates to the herbal extract having anti-viral activity. More specifically, it relates to the herbal extract produced by extracting the comminuted Fructus Ligustri Lucidi (privet fruit), Rhizoma Polygonati (sealwort), Herba Agrimoniae (agrimonia), Radix Rehmanniae Glutinosae Conquitae (steamed glutinous rehmannia) or the mixture thereof, with a low polar solvent, and to the method for in vitro antagonizing virus by contacting the herbal extract with viruses.

1 Claim, No Drawings

HERBAL EXTRACT HAVING ANTI-VIRUS ACTIVITY AND PREPARATION OF SAME

CROSS REFERENCES TO THE RELATED APPLICATIONS

This is a Continuation-in-part of pending U.S. application Ser. No. 11/518,252 filed Sep. 11, 2006, which is a divisional application of U.S. application Ser. No. 10/749,565 filed Jan. 2, 2004, abandoned.

BACKGROUND OF THE INVENTION (A) Field of the Invention

The invention relates to the herbal extract having anti-viral activity. More specifically, it relates to the herbal extract produced by extracting privet fruit, sealwort, agrimonia, steamed glutinous rehmannia or the mixture thereof, with a low polar solvent, and to the method for in vitro antagonizing virus by contacting the herbal extract with viruses.

(B) Description of Related Art

Viruses introduce a variety of diseases by spreading through different infection routes, such as air, droplet, or contact. Every year in spring and autumn, Taiwan is attacked by infectious diseases of digestive tract, which considerably affect the islands and threat the public, especially infants and children. Enteroviruses infect persons who make contact with oral or nasal secreta, excrement, or spray of patients. They are subject to spreading in places where high population density is available. Since no specific treatment has been found to conquer enterovirus infection, doctors often employ supporting treatment to defend from viruses. In addition, there exist a vast variety of changeable enteroviruses. Therefore, even if a person has been infected by a certain type of enterovirus, he or she obtains no life-long immunity to other types. The method to prevent from being infected by viruses is to wash hands whenever necessary, live in a clean and ventilated house, wear a respirator, and keep from contacting with infected persons.

The U.S. Pat. No. 6,214,350 relates to aqueous extracts from fruits of *Ligustrum lucidum* and/or *L. japonicum*. It reveals a method to prepare said extracts in the following steps: Fruits of *Ligustrum lucidum* and/or *L. japonicum* or mixture thereof are exposed to water to remove insoluble contents thereof; aqueous solution is acidified to get acid precipitate, which is then purified. Said patent reveals that said aqueous extracts from fruits of *Ligustrum lucidum* and/or *L. japonicum* may be used to treat Hepatitis B (HBV), Hepatitis C(HCV), and Human Immunodeficiency Virus (HIV).

The U.S. Pat. No. 5,888,527 relates to aqueous extracts from tea. Said extracts that contain active catechin and black tea polyphenols are used to antagonize fungus, bacteria, and influenza virus.

Until now, no publicized document has been found on how to obtain extracts from fruit of *Ligustrum lucidum* by using low polarity solvents, or how to use such extracts to antagonize viruses, especially enteroviruses, a subgroup of picornaviruses. In addition, since water is a high polarity substance and different viruses act differently and are considerably specific to medicines, none of the previous technologies illustrated hereinabove may be extended to either the concept or the implementation of the present invention. Moreover, there exists demand to prevent or treat viral diseases or symptoms with herbal medicines.

SUMMARY OF THE INVENTION

The present invention aims to provide an herbal extract having anti-viral activity by extracting privet fruit (Pharmaceutical name: Fructus Ligustri Lucidi; Botanical name: *Ligustrum lucidum* Ait), sealwort (Pharmaceutical name: Rhizoma Polygonati; Botanical name: *Polygonatum sibiricum* Red, *P. kingianum* Coll.et Hemsl, or *P. cvrtonema* Hua), agrimonia (Pharmaceutical name:Herba Agrimoniae; Botanical name: *Agrlmonla allosa* Ledeb), steamed glutinous rehmannia (Pharmaceutical name:Radix Rehmanniae Glutinosae Conquitae; Botanical name: *Rehmannia glutinosa* (Gaertn.) Libosch) or the mixture thereof, with at least one low polarity solvent.

Another objective of the present invention is to reveal a method to produce herbal extracts having anti-viral activity from privet fruit, sealwort, agrimonia, steamed glutinous rehmannia or the mixture thereof, with at least one low polarity solvent.

The third objective of the present invention is to reveal a method to antagonize virus in vitro by having said viruses exposed to herbal extracts having anti-viral activity in the present invention.

The present invention reveals a preferred embodiment wherein herbal extracts having anti-viral activity are used to antagonize viruses in vitro.

DETAILED DESCRIPTION OF THE INVENTION

The pharmaceutical names, botanical names, family names of the herbs used in the present invention is shown in Table 1.

TABLE 1

Herbs of the Present Invention

| Common Name | Pharmaceutical Name | Botanical Name | Family Name |
| --- | --- | --- | --- |
| Privet fruit | Fructus Ligustri Lucidi | *Ligustrum lucidum* Ait | Oleaceae |
| Sealwort | Rhizoma Polygonati | 1. *Polygonatum sibiricum* Red 2. *P. kingianum* Coll. et Hemsl 3. *P. cvrtonema* Hua | Liliaceae |
| Agrimonia | Herba Agrimoniae | *Agrlmonla allosa* Ledeb | Rosaceae |
| Steamed glutinous rehmannia | Radix Rehmanniae Glutinosae Conquitae | *Agrlmonla allosa* Ledeb | Rosaceae |
| Baical skullcap root | Radix Scutellariae | *Scutellaria baicalensis* Georgi | Labiatae |
| Phellodendron bark | Cortex Phellodendri | 1. *Phellodendron chinense* Schneidor 2. *P. amurense* Rupr. | Scrophulariaceae. |

Privet fruit (Fructus Ligustri Lucidi) is the fruit of the plant *Ligustrum lucidum* Ait. It belongs to the family of Oleaceae.

Sealwort (Rhizoma Polygonati) is the rhizome of the plant *Polygonatum sibiricum* Red, *P. kingianum* Coll.et Hemsl, or *P. cvrtonema* Hua. They belong to the family of Liliaceae.

Agrimonia (Herba Agrimoniae) is the aerial part or whole of the plant *Agrlmonla allosa* Ledeb. It belongs to the family of Rosaceae.

Steamed Glutinous Rehmannia (Radix Rehmanniae Glutinosae Conquitae) is the root of the plant *Rehmannia glutinosa* (Gaertn.) Libosch that has been cooked and then dried. It belongs to the family of Scrophulariaceae.

Baical skullcap root (Radix Scutellariae) is the dried root of the plant *Scutellaria baicalensis* Georgi. It belongs to the family of Labiatae.

Phellodendron bark (Cortex Phellodendri) is the dried bark of the plant *Phellodendron chinense* Schneidor or *P. amurense* Rupr. They belong to the family of Berberidaceae.

No specific instruction is necessary to illustrate the well-known steps as shown aforesaid, which are used to process crude herbal medicines and included in the present invention. The description of the present invention defines crude herbal medicines as but not limited to those obtained by following the aforesaid steps to process specific parts of plants, as well as crude herbal medicines obtained from the public or herbal stores.

Generally, extraction is one of the most common methods to take efficacy substances from herbal medicines. Common extractants include water, methanol, ethanol, and acetone, all of which feature on high polarity. Polarity is a structure-dependent physical characteristic of molecules and may be indicated by dipole moment and dielectric constant.

Water is a high polarity solvent with a dielectric constant around 80. It is powerful to penetrate herbal cells. The high polarity, in addition to hydrogen bond formation, leads to high boiling point and hardness for condensation. And, moreover, water extract is subject to molding. Also high on polarity, methanol, ethanol, and acetone, which are all hydrophilic solvents that can dissolve in water in any concentration, have dielectric constants about 31.2, 26.0, and 21.5. These solvents, again, demonstrate powerful penetrating to herbal cells. However, since the polarity is lower than that of water, the boiling points are also reduced. Lipophilic solvents are those hard or definitely not able to dissolve in water, such as light Petroleum Ether (dielectric constant≈4.8), benzene (dielectric constant≈2.3), ether (dielectric constant≈4.3), chloroform (Dielectric constant≈5.2), and ethyl acetate (dielectric constant≈6.1). These solvents have low boiling points and weak penetrating to herbal cells.

The present invention uses a low polarity solvent as the extractant, instead of high polarity solvents (such as water) used in previous technologies, to produce anti-viral extracts from privet fruit, sealwort, agrimonia, steamed glutinous rehmannia. The present invention includes any of the aforesaid herbal medicines, as well as mixtures of more than one medicine thereof.

The present invention aims to provide an herbal extract having anti-viral activity by extracting privet fruit, sealwort, agrimonia, steamed glutinous rehmannia or the mixture thereof, with at least one low polarity solvent.

To deliver better extraction result, one or more of the aforesaid herbal medicines should be physically made to particles as tiny as possible before the extraction revealed in the present invention, by pounding, grinding, or cutting. To facilitate extracting, it is preferred to grind one or more of the aforesaid herbal medicines into small particles, or, for the best, into powders.

The description of the present invention defines the term of "Low Polarity" solvent as a solvent with a dielectric constant less than 10, which includes but not limit to ethyl acetate, dichloromethane, chloroform, carbon tetrachloride, cyclohexane, normal hexane, normal butyl alcohol, benzene, or the mixture thereof.

A preferred embodiment of the present invention uses a low polarity solvent of dichloromethane, normal hexane, or normal butyl alcohol.

Before proceeding with the extraction step revealed in the present invention, a pre-extraction step with methanol, ethanol or the mixture thereof may be performed as necessary on one or more of the aforesaid crude herbs that has been comminuted beforehand. The aforesaid description has indicated that both methanol and ethanol are high polarity hydrophilic solvents with dielectric constants between 26 and 31. However, since substances in herbal cells, except for protein, grease, and wax, can more or less dissolve in methanol or ethanol, the aforesaid pre-extraction step that uses methanol or ethanol (or mixture thereof) as the extractant will assist in the later extraction step, where a low polarity solvent will be used, as revealed in the present invention.

Substances extracted from one or more of the aforesaid crude herbs by using a low polarity solvent may be prepared for a wide range of applications. Various steps may be followed to purify the aforesaid substances as necessary when the extraction step revealed in the present invention is completed. It is not necessary to give any specific instructions on said purification, which is well-known for most specialists in the area.

Methods for said purification include: chromatography, crystallization, filtration, and sedimentation. Choices should be made according to the purpose of said purification.

A preferred embodiment of the present invention includes a step to purify substances extracted from one or more of the aforesaid crude herbs by using a low polarity solvent. The aforesaid embodiment employs, for example, a filtration method to remove insoluble contents. Another preferred embodiment of the present invention employs silica gel on the purification step, with dichloromethane and ethyl acetate being used as extracting agents.

Another objective of the present invention is to reveal a method to produce herbal extracts having anti-viral activity from privet fruit, sealwort, agrimonia, steamed glutinous rehmannia or the mixture thereof, with at least one low polarity solvent. Before proceeding with the extraction step, a pre-extraction step may be performed with methanol, ethanol or the mixture thereof as necessary. Again, a purification step may be performed on substances extracted with low polarity solvent(s) to obtain purified efficacious contents.

The third objective of the present invention is to reveal a method to antagonize virus in vitro by having said viruses exposed to herbal extracts having anti-viral activity prepared in the present invention.

The description of the present invention specifically defines the term of "virus" as any virus of picornaviruses, preferably to enteroviruses, and more preferably to enterovirus type 71.

Herbal extracts having anti-viral activity in the present invention may be used after and/or without being purified, or more preferably, used with carriers, diluents, excipient, or adjuvant that are traditionally employed to make up prescriptions. For that purpose, they may be emulsifiable condensates shaped in appropriate and well-know manners, such as soap bath, detergent, washing powder, or shampoo; mash that may be used for coating, such as paints; solutions that may be sprayed directly, such as nebulae; diluted solutions, such as beverage and healthful foods; contents that may be used to fill certain objects, such as toys and wiping rags; dissolvable powder, dust, or particles; or substances that may be enclosed in appropriate wraps, such as air filters, water filter elements, contents of masks, or filtration membranes. If they are to be used as combinations, they may be processed based on the purpose and key surrounding conditions for applications, for example, by sprinkling, nebulizing, spraying, disseminating, coating, or emulsifying. Combinations may contain additional adjuvant, such as stabilizers, antifoam agents, viscosity modifiers, tackifiers, or other recipes for special effects.

Herbal extracts having anti-viral activity in the present invention are usually used as combinations. Said substances may also be used simultaneously or in sequence with other substances, such as other anti-viral drugs or their mixtures or nourishment ingredients, in order to deliver enhanced anti-viral activity and improved efficacy.

Herbal extracts having anti-viral activity in the present invention may be used as necessary to prepare a combination of multiple drugs which has the efficacy to treat or prevent from viruses (preferably to enteroviruses, and more preferably to enterovirus type 71). Said combination may be used to treat or prevent from minor or severe enterovirus infections. Herbal extracts having anti-viral activity in the present invention may be used independently or in combination with medically acceptable carriers or excipient for medication in single or multiple dosages. Medically acceptable carriers or diluents or any other known adjuvant and excipient may be prepared with traditional techniques. Refer to *Remington's Pharmaceutical Sciences*, the $19^{th}$ Edition, Edited by Gennaro, Mack Polishing House, Easton, Pa. (1995).

The aforesaid combination of multiple drugs may be prepared in specific manners for appropriate medication approaches, such as by oral administration or through recta, nasal cavity, lungs, face (including cheek and sublingual), skin, cistern, inner peritoneum, vagina, and non-digestive tracts (including subcutaneous tissue, inner muscle, inner spinal canal, inner vein, and intracutaneous tissues). It is necessary to note that the best medication approach should be determined based on the normal symptom, the age of the patient to be treated, characteristics of the symptom to be cured, and the selected active contents.

The aforesaid combination of multiple drugs may be prepared into solid states, such as capsule, tablets, sugarcoated tablets, pills, powder, and particles. By using well-known techniques, said combination may be prepared along with tablet coats (such as enteric coats), or so prepared to control the releasing of active contents, for example, to release continuously or slowly, whenever appropriate.

Liquors for oral administration may be of solution, emulsion, suspension liquid, syrup medicines, and elixir.

Combinations of multiple drugs for medication in non-digestive tracts include injection of sterilized-water/water-free solution, dispersing agents, suspension liquid, emulsion, and sterilized powder that should be dissolved in sterilized injection or dispersing agent before usage.

There are also some other medication methods, such as suppository, spraying medicine, ointment, frost agent, gelatin, inhalation, skin patch, and implantation materials, etc.

The actual dosage of the herbal extracts having anti-viral activity in the present invention should be determined based on the medication frequency and method, the sex, age, body weight, and general status of the patient to be treated, characteristics and severity of the symptom to be cured, and complications.

A number of embodiments are given as follows to detail the present invention, without any intention to limit the claims of said invention.

EMBODIMENT 1

Preparing Extracts from Privet Fruit 1.5 kg fresh privet fruit sourced from a normal market are pre-extracted with ethanol in room temperature for six cycles (2 kg for each). 12 kg ethanol is removed to obtain 403 g pre-extract. The pre-extract from said pre-extraction is further extracted with 1-2 kg dichloromethane. Then, dichloromethane is removed to gain 191 g extract. The extract from said extraction is injected into a column packed with silica gel and the eluted with dichloromethane/ethyl acetate solution (10:1-1:5) as the eluting agent. Then, solvent from the elute solution is removed to finally obtain 80 g extract (dry powder) from privet fruit.

EMBODIMENT 2

Preparing Extracts from Sealwort

The steps are identical to that of the aforesaid Embodiment 1. sealwort with an amount equal to that of privet fruit in said Embodiment 1 is extracted and purified with normal hexane to prepare extract from sealwort in the present invention.

EMBODIMENT 3

Preparing Extracts from Agrimonia

The steps are identical to that of the aforesaid Embodiment 1. agrimonia with an amount equal to that of privet fruit in said Embodiment 1 is extracted and purified with normal hexane to prepare extract from agrimonia in the present invention.

EMBODIMENT 4

Preparing extracts from steamed glutinous rehmannia

The steps are identical to that of the aforesaid Embodiment 1. steamed glutinous rehmannia a with an amount equal to that of the fruit of privet fruit in said Embodiment 1 is extracted and purified with dichloromethane and normal butyl alcohol solution to prepare extract from steamed glutinous rehmannia in the present invention.

EMBODIMENT 5

Culturing Cells

Rhabdomyosarcoma (RD) cells (sourced from Virus Lab of Chang Gung Hospital) are added into DMEM (Gibco) solution containing 10% fetal bovine serum. Said culture solution is placed in a 37° C. incubator which contains 5% $CO_2$ to culture said cells. To proceed with subculture, 1× phosphate buffer solution (PBS) is used to wash the cells twice. Then, appropriate amount of 0.25% trypsin-EDTA (Gibco) is added to process said cells. When said cells fall off the surface of the culture dish, DMEM solution containing 10% fetal bovine serum is added. The solution is stirred to have said cells evenly distributed within the dish. The dish is placed in a 37° C. incubator containing 5% $CO_2$ to culture said cells.

EMBODIMENT 6

Culturing Viruses

Enterovirus 71/Tw/2231/98 (sourced from Virus Lab of Chang Gung Hospital) is diluted with culture solution free of fetal bovine serum. RD cells are cultured in DMEM solution containing 10% fetal bovine serum. When about 90% of the dish is filled with said cells, clean them with 1×PBS for once. Then said diluted virus solution is added. The mixture is placed in a 35° C. incubator which contains 5% $CO_2$ for absorption for 1 hour. Then DMEM solution containing 2% fetal bovine serum is added. The mixture is placed in a 35° C. incubator wherein 5% $CO_2$ is available to culture said viruses. When cytopathy of rounding and falling off is observed on more than 95% of said cells, the supernatant is collected, centrifugally processed, frozen, unfrozen, and stored in a −80° C. refrigerator.

EMBODIMENT 7

Toxicity Testing

The cells cultured in said Embodiment 5 are placed on a 96-hole cell-culturing dish and then mixed with the drug to be tested. The mixture is left for 1 hour before DMEM solution containing 2% fetal bovine serum is added. The mixture is placed in a 35° C. incubator which contains 5% $CO_2$ to culture said cells for 3-4 days. Before reading, 5% formalin is added to fix the status for 1-2 hours. Then 0.1% crystal violet (J. T. Baker) is added to dye said cells for 2-3 minutes. After the cells are washed with water, the $OD_{570\ nm}$ value is measured.

EMBODIMENT 8

Neutralization Test

The cells cultured in said Embodiment 5 are placed on a 96-hole culture dish. A specific amount of virus solution is mixed with the extract to be tested. The mixture is added into the culture solution for one-hour absorption. Then DMEM solution containing 2% fetal bovine serum is added. The mixture is placed in a 35° C. incubator which contains 5% $CO_2$ to culture said cells for 3-4 days. Before reading, 5% formalin is added to fix the status for 1-2 hours. Then 0.1% crystal violet (J. T. Baker) is added to dye said cells for 2-3 minutes. After the cells are washed with water, the $OD_{570\ nm}$ value is measured.

REFERENCE EMBODIMENT

In order to comparing with the Embodiment 1, Sealwort, agrimonia, steamed glutinous rehmannia, baical skullcap root and phellodendron bark are pre-extracted with ethanol in room temperature for six cycles (2 kg ethanol for each cycle) as shown in the Embodiment 1, and then extracted the pre-extract with a high polarity solvent: water.

In addition, privet fruit are pre-extracted with ethanol in room temperature for six cycles (2 kg ethanol for each cycle) as shown in the Embodiment 1, and then extracted with methanol. Then, ethyl acetate:water (1:1) solution is used for separating two layers, to obtain extract in both organic and aqueous phases.

Neutralization test is performed as per said Embodiment 5 to measure the viral-inactivating efficacy of herbal extracts obtained in said Embodiments 1-4 and said reference embodiment of the present inventory.

Said neutralization test indicates that enterovirus type 71 is inactivated by 45% when it is immersed in an extract 0.66 mg/ml in concentration that is prepared from privet fruit in the present invention by using dichloromethane. Inactivating efficacy is also observed from other extracts prepared in the present invention with low polarity solvents. For example, it is observed that the enterovirus type 71 is inactivated when it's immersed in an extract 0.1-0.25 mg/ml in concentration that is prepared from steamed glutinous rehmannia by using dichloromethane/normal butyl alcohol, an extract 0.1-0.5 mg/ml in concentration from sealwort. using normal hexane, or an extract 0.125-0.25 mg/ml in concentration from agrimonia using normal hexane. As compared to extracts prepared by using other high polarity solvents, the extracts obtained in the present invention demonstrate remarkable anti-viral activity. In order make comparison with previous US patents wherein water is used as the extractant, the aforesaid reference embodiment of the present invention also employs water to extract privet fruit No inactivating efficacy has been found against enterovirus type 71 in water-soluble extracts from privet fruit.

Moreover, the toxicity testing shows that the extract prepared in the present invention by extracting fruit of privet fruit has a 50% fatal dose ($LC_{50}$) of 0.247 mg/ml against RD cells. That is, RD cells can endure a higher dose of said extracts than that of others.

It may be concluded from the foresaid testing results that the herbal extracts prepared in the present invention are substantial to antagonize enterovirus, especially enterovirus type 71. Therefore, said herbal extracts may be used on materials capable of absorbing viruses thereupon, such as air filters, filtration membranes, masks, soap bath, water filters, coatings, and wiping rags. Since said materials may absorb viruses thereupon, human bodies are protected from infectious contacting with said viruses. Even more, substances having anti-viral activity are also available on said materials to inactivate viruses—an inactivated virus has no way to infect human bodies. In such a way, routes for viruses to spread are blocked. Since the present invention delivers considerable assistance to fight against spreading viruses, industrial application is available. Since the present invention demonstrates remarkable potentials to assist in the fighting against spreading viruses, industrial applicability is available.

The preferred embodiments revealed hereinabove in the present invention are not intended to limit said invention. It is apparent for those skilled in the art that various changes and modifications may be made therein without departing from the spirit or scope of this invention. The scope of protection for the present invention shall be considered as those specified in the claims hereinafter.

What is claimed is:

1. A method of inactivating enterovirus type 71 in vitro, comprising contacting enterovirus type 71 with an herbal extract in vitro ; wherein said herbal extract is prepared by:
    a) pre-extracting comminuted Fructus Ligustri Lucidi (privet fruit) with a solvent selected from the group consisting of methanol, ethanol and a mixture thereof to obtain a pre-extract,
    b) extracting said pre-extract of step (a) with dichloromethane to obtain an extract,
    c) purifying the extract of part (b) by passing said extract through a column packed with silica gel,
    d) eluting the column with dichloromethane/ethyl acetate to obtain an eluate; and
    e) removing solvent from the eluate to obtain a powder which is the herbal extract.

* * * * *